US012661432B2

(12) United States Patent
Lewandowska-Łańcucka et al.

(10) Patent No.: US 12,661,432 B2
(45) Date of Patent: Jun. 23, 2026

(54) MULTIFUNCTIONAL, HYDROGEL HYBRID MATERIAL, THE METHOD OF ITS PREPARATION AND THE USE IN THE TREATMENT OF BONE LOSSES

(71) Applicant: Uniwersytet Jagielloński, Cracow (PL)

(72) Inventors: Joanna Lewandowska-Łańcucka, Wolbrom (PL); Maria Nowakowska, Cracow (PL); Adriana Gilarska, Łowce (PL)

(73) Assignee: Uniwersytet Jagielloński, Cracow (PL)

( * ) Notice: Subject to any disclaimer, the term of this patent is extended or adjusted under 35 U.S.C. 154(b) by 574 days.

(21) Appl. No.: 18/023,423

(22) PCT Filed: Aug. 26, 2021

(86) PCT No.: PCT/PL2021/050060
§ 371 (c)(1),
(2) Date: Feb. 27, 2023

(87) PCT Pub. No.: WO2022/045910
PCT Pub. Date: Mar. 3, 2022

(65) Prior Publication Data
US 2023/0310714 A1      Oct. 5, 2023

(30) Foreign Application Priority Data

Aug. 26, 2020    (PL) ........................................ 435104

(51) Int. Cl.
*A61L 27/52*        (2006.01)
*A61L 27/46*        (2006.01)
*A61L 27/54*        (2006.01)

(52) U.S. Cl.
CPC ............... *A61L 27/52* (2013.01); *A61L 27/46* (2013.01); *A61L 27/54* (2013.01); *A61L 2400/06* (2013.01)

(58) Field of Classification Search
CPC ....................................................... A61L 27/46
See application file for complete search history.

(56) References Cited

FOREIGN PATENT DOCUMENTS

PL          428993      *   8/2020    .............. A61P 27/46

OTHER PUBLICATIONS

International Search Report and the Written Opinion Dated Dec. 23, 2021 From the International Searching Authority Re. Application No. PCT/PL2021/050060. (14 Pages).
Gilarska et al. "Bioactive Yet Antimicrobial Structurally Stabel Collagen/Chitosan/Lysine Functionalized Hyaluronic Acid—Based Injectable Hydrogels for Potential Bone Tissue Engineering Applications", International Journal of Biological Macromolecules, XP055868097, 155: 938-950, Published Online Nov. 9, 2019 . . . .
Lewandowska-Lancucka et al. "Genipin Crosslinked Bioactive Collagen/Chitosan/Hyaluronic Acid Injectable Hydrogels Structurally Amended Via Covalent Attachment of Surface-Modified Silica Particles", International Journal of Biological Macromolecules, XP085753760, 136: 1196-1208, Published Online Jun. 25, 2019.

* cited by examiner

*Primary Examiner* — Paul V Ward

(57) ABSTRACT
A multifunctional hydrogel hybrid material and a method of its preparation and use in the treatment or prophylaxis of bone tissue loss is disclosed.

7 Claims, 13 Drawing Sheets

MULTIFUNCTIONAL, HYDROGEL HYBRID MATERIAL, THE METHOD OF ITS PREPARATION AND THE USE IN THE TREATMENT OF BONE LOSSES

RELATED APPLICATIONS

This application is a National Phase of PCT Patent Application No. PCT/PL2021/050060 having International filing date of Aug. 26, 2021, which claims the benefit of priority of Poland Patent Application No. P.435104 filed on Aug. 26, 2020. The contents of the above applications are all incorporated by reference as if fully set forth herein in their entirety.

FIELD AND BACKGROUND OF THE INVENTION

The invention relates to a multifunctional hybrid material with therapeutic potential, a method for preparation of such hydrogel materials, and their use in regenerative medicine, in particular in the treatment of bone losses caused by osteoporosis.

The present invention relates to a multifunctional, inject-able hydrogel hybrid material useful for the reconstruction of bone tissue, in particular minor bone losses caused by osteoporosis. The material can be precisely and in minimally invasive manner introduced into the loss site, where it will form a scaffold for the reconstruction of bone tissue. Composition of this material enables its biointegration, creates a convenient biomatrix for colonization by osteoblastic cells (biomimetic composition), has the desired mechanical properties (polymer matrix enriched with the mineral phase), and also has a high therapeutic potential (the presence of silica-apatite particles with an attached drug—alendronate). Bio-polymer scaffolds constructed in this way, chemically cross-linked with a substance of natural origin, additionally serve as a system for controlled, localized delivery of an active substance (alendronate), that plays a key role in the treat-ment of osteoporosis at the site of bone tissue damage. The presented solution ensures a non-invasive placement of the scaffold at the site of implantation, while maintaining the structure and biological properties, as well as limiting poten-tial adverse side effects of the therapy.

Various types of alendronate carriers are described in the literature, including nanoparticles [Posadowska, U., et al., (2015), Int. J. Pharm, 485 (1-2), 31-40], microcapsules [Mondal, T. et al., (2012), Mater. Sci. Eng. C, 32 (4), 697-706], bone cement [van Houdt, Cl, et al., (2018), Sci Rep, 8 (1), 1-13], mesoporous materials [Cicco, S R, et al., (2019), Mater. Sci. Eng. C, 104, 109897; Manzano, M., et al., (2009), Expert Opin. Drug Deliv, 6 (12), 1383-1400], thermosensitive chitosan hydrogels [Nafee, N., et al., (2018), J. Drug Target, 26 (7), 563-575], or hydrogel hybrid materials such as collagen-hydroxyapatite [Ma X., et al., Colloids Surf B Biointerfaces 143 (2016) 81-87].

In a paper by Larsen, C., et al., (2009), Expert Opin. Drug Deliv, 6 (12), 1283-1295, a literature review was made, which disclosed the possibility of using mesoporous silica as a carrier for alendronate. The performed research included application of various types of mesoporous matrices, as well as their modification with aminopropyl groups. It has been shown that the load of the drug in the mesoporous matrix increases with increasing surface area of the material. It was also revealed that the presence of amino groups in the modified mesoporous silica significantly improves the drug loading efficiency, which is explained as the effect of strong interactions between the matrix amino groups and alendro-nate phosphate groups.

In the paper by Cicco, S. R., et al., (2019), Mater. Sci. Eng. C, 104, 109897 it has been shown that the presence of mesoporous bio-silica inhibits the cytotoxic effect of alen-dronate itself. However, the proposed model system (mate-rial on the substrate), does not ensure local implantation in a non-invasive manner.

A paper by Ma X., et al., Colloids Surf B Biointerfaces 143 (2016) 81-87 disclosed a two-step process for prepara-tion of biomimetic hybrid hydrogels as potential tissue engineering scaffolds, containing collagen, hydroxyapatite and alendronate. The alendronate coated hydroxyapatite (4.0 wt %) was suspended in genipin cross-linked collagen under physiological conditions. The authors prepared the HAp-ALN system taking advantage of the described in the literature affinity of the drug to hydroxyapatite, [Neamtu, J., et al., (2017), J. Therm. Anal. Calorim, 127 (2), 1567-1582], whereby they used commercially available HAp. Improve-ment in mechanical properties was observed, as well as an absence of cytotoxic effect against the MG-63 osteoclastic cell line. The work does not disclose any studies that would show a therapeutic effect as well as an improved biointe-gration.

The Polish patent application No. P.428993 describes a method for preparation of a hydrogel hybrid material con-taining particles of silica with surface modified with amino groups, dispersed in a mixture of biopolymers (collagen, chitosan, hyaluronic acid in the weight ratio 50:40:10), and cross-linked with genipin. To obtain this material, commer-cially available hyaluronic acid was used (it was not sub-jected to any modifications) and it accounted for 10% by weight of the biopolymer mixture. The material did not contain alendronate as a part of the composition, and had no therapeutic properties.

Process of reconstruction of bone tissue determines the proper functioning of the skeletal system, and thus of the entire organism. The process is initiated when the continuity of canaliculies formed by the cytoplasmic processes of osteocytes, and connecting osteocytes with each other and with resting osteoblasts (the so-called lining cells) is broken (microfracture formation). Consequently, osteocyte apopto-sis occurs, which is also a signal to the lining cells about the location and extent of tissue damage. In the next step, the lining cells release local factors, posing a signal to the osteoclast precursor cells to start the process of migration to the damaged site, and differentiation into osteoclasts (osteo-clastogenesis). Mature osteoclasts resorb the bone matrix along with the microfracture, forming the so-called a resorp-tion cavity. This phase, called the resorption phase, lasts about 2-4 weeks and ends with osteoclast apoptosis. The step is followed by a short recovery phase, during which the resorption cavity is re-lined with bone forming cells (osteo-blasts). Then, the bone formation phase, lasting about 4-6 months, takes place during which osteoblasts produce an osteoid, which is gradually mineralized, resulting in filling the loss with fully mineralized bone.

Osteoporosis is a disease in which the balance of resorp-tion and bone formation processes is disturbed, which in turn leads to increased resorption and acceleration of bone turn-over. In addition, as the body ages, the bone formation processes become less efficient, which leads to lesser amount of bone being formed and an increased amount of bone being resorbed. This means that with each cycle of internal bone reconstruction, some bone tissue is removed, resulting in loss of bone mass and damage to its structure. As a result, bone turnover is intensified—more resorption cavities are created on a given surface at a given moment, and the bone mineralization time is shortened. The most commonly used group of drugs in the treatment of osteoporosis (in postmenopausal women, corticosteroid-induced osteoporosis) are bisphosphonates, in particular nitrogen bisphosphonates, e.g. sodium alendronate, ALN, which, due to their affinity to the bone mineral (hydroxyapatite), are characterized by high selectivity towards the bone tissue.

The main goal of these drugs is to normalize the excessive resorption activity of osteoclasts, and increased bone turnover. Nitrogen bisphosphonates lead to the death of the osteoclast cell as a result of inhibition of farnesyl diphosphate synthase (FPP—an enzyme of the mevalonate pathway), the primary role of which is production of substrates for the synthesis of key compounds for normal cellular metabolism. As a result, the osteoclast cytoskeleton, membrane folding and carrier vesicle movement are disturbed, leading to loss of osteoclast resorptive activity, and in consequence to the cell apoptosis. Preclinical studies have shown that the drug has no direct effect on the bone formation process, and the bone tissue produced during treatment with alendronate shows normal structure. The drug is most often administered orally, which unfortunately is associated with numerous side effects (osteonecrosis of the jaw, irritation of the gastrointestinal system, nausea). Intravenous administration of ALN, apart from the side effects in the form of fever, flu-like symptoms and electrolyte imbalance, also carries the risk of nephrotoxicity due to the formation of complexes with calcium and accumulation in non-calcified tissues. Therefore, a system enabling local administration and thus localized action of this drug seems to present an extremely attractive solution, ensuring suppression of bone resorption and at the same time limiting the systemic side effects during the whole therapy.

Satisfying the growing demand for multifunctional biomaterials for tissue engineering, possessing specific physical, chemical and biological properties, faces limitations related to complicated production procedures and high production costs. This creates technical problems between laboratory testing and therapeutic applications.

SUMMARY OF THE INVENTION

Providing a multifunctional hydrogel hybrid material suitable for use in tissue engineering, which have a therapeutic effect, i.e. inhibits activity of osteoclasts and at the same time does not inhibit activity of osteoblasts, while the desired hydrogel material should undergo rapid biomineralization, preferably after a few days after administration, which would enable its faster biointegration with bone tissue, and support the bone formation process, as well as a method for preparation of the said material, constitutes the technical problem.

The present invention was aimed at development and production of multifunctional, hydrogel hybrid material that would be characterized by:

therapeutic potential allowing inhibition of osteoclastic cells, bioactivity depending on rapid bio-integration of the material with the bone and supporting the bone mineralization process, especially the bone mineralization process disturbed by osteoporosis, a biomimetic composition that provides an environment favorable for functioning of osteoblasts, injectability enabling non-invasive and localized administration of the material in the form of a sol, into the bone loss, and ability to cross-link under physiological conditions.

Unexpectedly, the goal defined above was achieved by the present invention.

The invention relates to a multifunctional hybrid material with therapeutic potential, characterized in that it contains:

a) a biopolymer matrix containing: collagen, chitosan, hyaluronic acid, preferably said hyaluronic acid is modified with lysine, b) silica-apatite particles functionalized with amino groups, c) the active substance in the form of alendronate attached to silica-apatite particles, d) a cross-linking substance.

Preferably, the biopolymer matrix contains: collagen, chitosan, modified hyaluronic acid in the weight ratio 5:2:3, respectively.

Preferably, the hyaluronic acid is modified with lysine.

Preferably, the cross-linking substance is genipin.

A method of producing of the multifunctional hydrogel hybrid material constitute another object of the invention, and is characterized in that it comprises the following steps:

a) the silica particles are functionalized with amino groups, b) the particles obtained in step a) are suspended in an aqueous SBF solution, preferably at a concentration of 1.5 M, to obtain, after 10 days of incubation, the silica particles coated with the mineral phase, c) using its affinity for apatite, sodium alendronate is bonded to the particles obtained in the step b), d) a solution of collagen, chitosan and lysine-modified hyaluronic acid is added to the aqueous suspension of the particles of the step c), e) the mixture obtained in step d) is subjected to a cross-linking reaction with genipin.

Preferably, the process according to the invention is carried out by the sol-gel method.

Another embodiment of the invention relates to the multifunctional hydrogel hybrid material as defined above or obtained by the method as defined above, for use in the treatment or prophylaxis of bone losses. Preferably, the bone losses are due to osteoporosis.

BRIEF DESCRIPTION OF THE SEVERAL VIEWS OF THE DRAWINGS

For a better understanding of the essence of the invention, the present description is illustrated with the accompanying figures.

DESCRIPTION OF SPECIFIC EMBODIMENTS OF THE INVENTION

Figure 1:
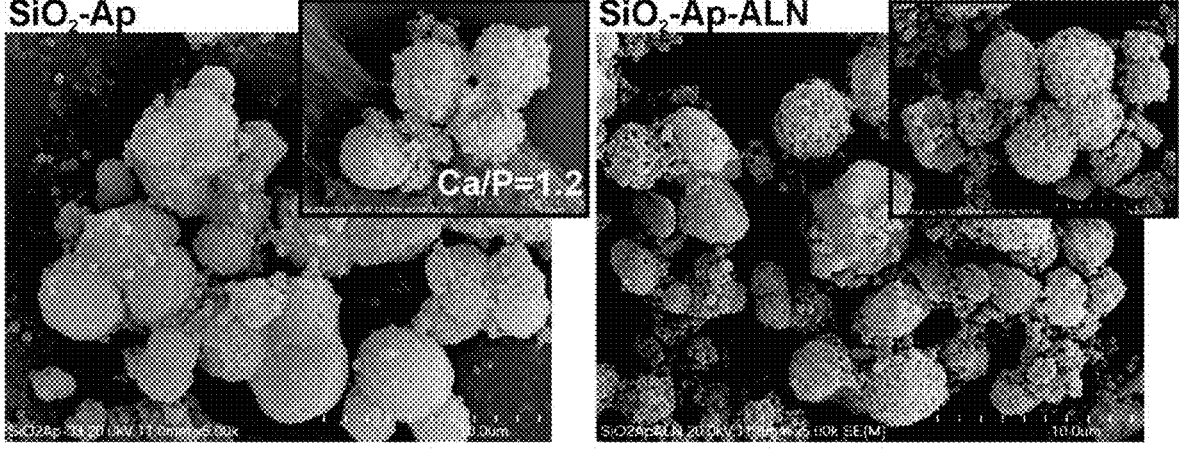
FIG. 1 shows the SEM microphotographs of $SiO_2$-Ap and $SiO_2$-Ap-ALN submicron particles.

Moreover, the essence of the invention is explained in the following examples.

Examples 1, 2 and 4 disclose consecutive steps of an exemplary implementation of the method according to the invention, while Examples 3 and 5 disclose properties of the materials obtained according to the invention.

Example 1. Preparation of SiO$_2$-Ap Submicron Mineral Particles

Controlled deposition of apatite (Ap) on the surface of the silica particles was performed in contact with artificial plasma (1.5 SBF).

Preparation of the Artificial Plasma

For this purpose, 1000 mL of 1.5 SBF were prepared. 700 mL of deionized water was added to a 1000 mL plastic beaker. The beaker was placed on a magnetic stirrer in a water bath at 36.5±1.5° C. Reagents 1 to 8 were dissolved following the order shown in Table 1 (the next reagent was added after the previous one had completely dissolved). Deionized water was added to a volume of 900 mL and temperature of the solution was set again to 36.5±1.5° C. Then the pH control was started, for this purpose the electrode of the pH meter was placed in the solution. In the next step, Tris was dissolved in the solution, with constant control of pH, by adding small portions of the reagent. When the pH came to 7.30±0.05, the temperature was checked to maintain it within 36.5±1.5° C. After checking the temperature, Tris was added again, to raise the pH to 7.45. When the pH rose to 7.45±0.01, the dissolution of the Tris was stopped and 1 M HCl was added to bring the pH down to 7.42±0.01, taking care not to drop the pH below 7.40. After lowering the pH to 7.42±0.01, the remaining Tris was dissolved without exceeding a pH of 7.45. After all the Tris had dissolved, the temperature of the solution was adjusted to 36.5±0.2° C. The pH of the solution was adjusted by dropwise addition of 1 M HCl to 7.42±0.01 at a temperature of 36.5±0.2° C. The pH was finally adjusted to 7.40 at 36.5° C. The solution was then poured into a plastic flat bottom flask, made up to 1000 mL and stored in a refrigerator.

TABLE 1

Reagents and their amounts needed to prepare 1000 mL of 1.5 SBF

| no | reagent | mass/volume |
|----|---------|-------------|
| 1 | NaCl | 12.0525 g |
| 2 | NaHCO$_3$ | 0.5325 g |
| 3 | KCl | 0.3375 g |
| 4 | K$_2$HPO$_4$•3H$_2$O | 0.3465 g |
| 5 | MgCl$_2$•6H$_2$O | 0.4665 g |
| 6 | 1.0M HCl | 58.5 mL |
| 7 | CaCl$_2$ | 0.438 g |
| 8 | Na$_2$SO$_4$ | 0.108 g |
| 9 | Tris | 9.117 g |
| 10 | 1.0M HCl | 0-7.5 mL |

Deposition of Apatite (Ap) on the Surface of Amine-Functionalized Silica Particles Amine-functionalized silica particles were obtained by the sol-gel method according to the procedure described in [J. Lewandowska-Łańcucka et al., Int. J. Biol. Macromol. 136 (2019) 1196-1208] as follows: 1.0 mL of tetraethoxysilane (TEOS) and 0.1 mL of aminopropyltriethoxysilane (APTES) were sequentially added to a mixture of ethanol (5.1 mL) and water (5 mL). The resulting mixture was left on a magnetic stirrer and stirred for 30 min at room temperature. The material obtained in this way was subjected to the centrifugation process and then it was cleaned by washing with ethanol and centrifugation. The washing in ethanol/centrifugation cycle was repeated four times. The material was dried in a vacuum oven at 60° C. After purification, a white powder ($SiO_2$—$NH_2$) was obtained.

In the next step, 20 mg of $SiO_2$—$NH_2$ particles was placed in 50 mL vials and 20 mL of 1.5 M SBF solution was added. The samples were sonicated continuously for 10-15 minutes. The vials were then protected with Parafilm and placed in an incubator set at 37° C. and shaken (50 rpm). The materials prepared in this way were incubated for a period of 10 days, replacing the SBF solution with the fresh one every 2-3 days. For this purpose, the suspension of particles in SBF was centrifuged at 10,000 rpm for 5 minutes, the supernatant was removed, a fresh aliquot of buffer was introduced, vortexed and incubated again. After a 10-day incubation in artificial plasma, the material was centrifuged, then cleaned by washing with water and centrifugation (the procedure was repeated three times), and then dried at room temperature. The material ($SiO_2$-Ap) was obtained in the form of a white powder.

Example 2. Preparation of the Submicron Bioactive Mineral Particles Carrying Alendronate ($SiO_2$-Ap-ALN)

Sodium alendronate was attached to the $SiO_2$-Ap system obtained as a result of controlled deposition under SBF conditions. For this, 20 mg of the $SiO_2$-Ap material was suspended in 3 mL of sodium hydroxide (5 mM) and sonicated for 5 min. Then 4 mg of sodium alendronate (ALN) was dissolved in 2 ml of NaOH solution (5 mM). The electrode of the pH-meter was placed in the solution and the pH was adjusted to 10 by adding NaOH (20 mM) solution. Then the sodium alendronate solution prepared in this way was added to the $SiO_2$-Ap suspension. The sample was placed on a magnetic stirrer with heating function (500 rpm, 37° C.) for 3 days. The resulting alendronate attached material ($SiO_2$-Ap-ALN) was purified by dialysis into water (24 hours, room temperature) and lyophilized to give a white powder.

Example 3. Physicochemical Properties of the Submicron Mineral Particles ($SiO_2$-Ap) and the Submicron Bioactive Mineral Particles Carrying Alendronate ($SiO_2$-Ap-ALN)

The particles obtained in examples 1 and 2 were characterized in detail using a number of physicochemical techniques—the morphology (SEM) as well as the chemical composition (EDS, XRD, XPS, TG) were determined. SEM and EDS studies (FIG. 1) showed the presence of a mineral phase with the morphology and composition (Ca/P ratio=1.2) characteristic of apatite structures.

Figure 2:
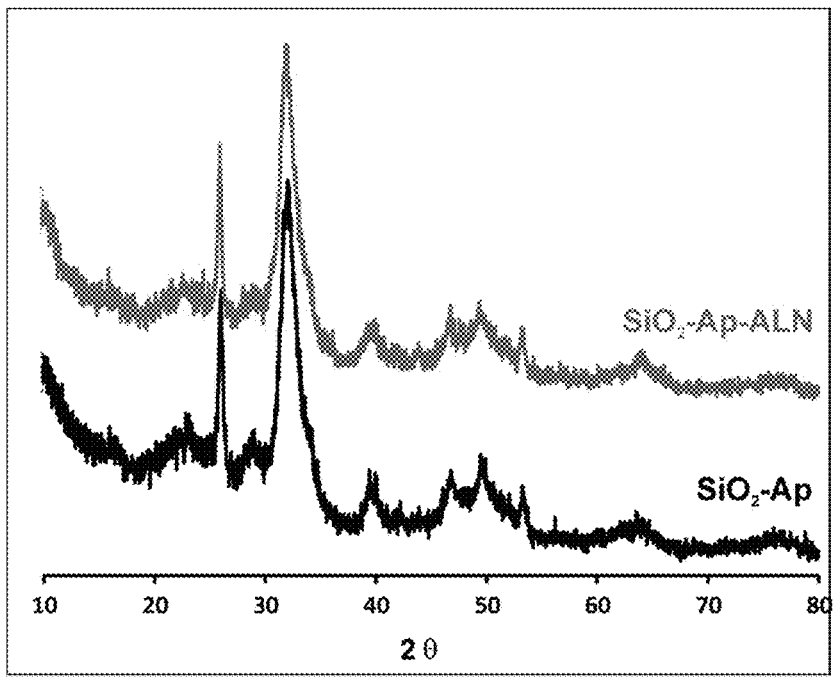
FIG. 2 summarizes the diffractograms of $SiO_2$-Ap and $SiO_2$-Ap-ALN particles.
Figure 3:
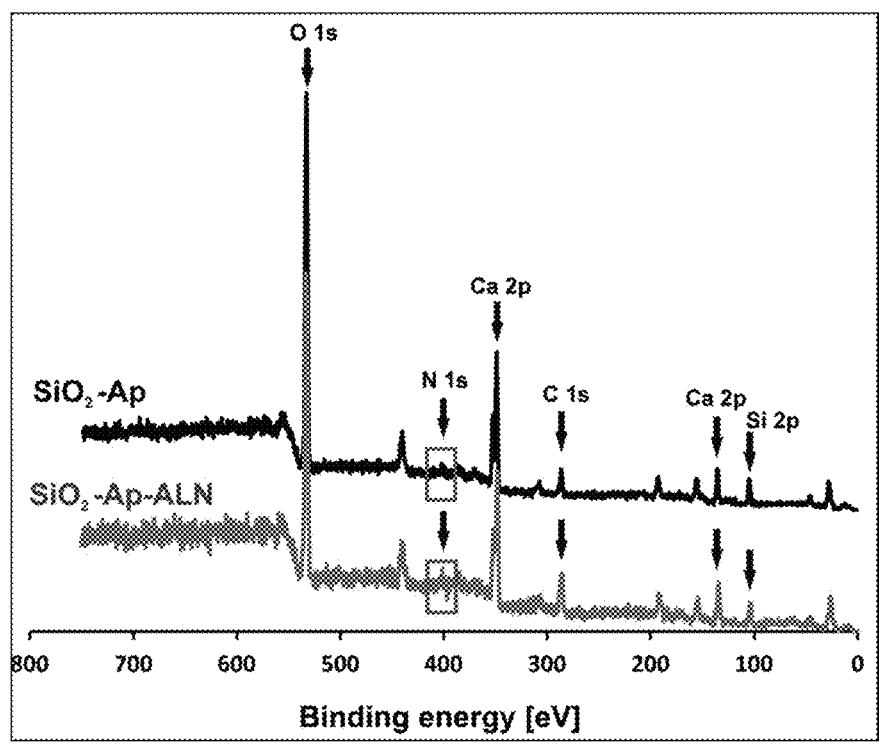
FIG. 3 summarizes XPS spectra of $SiO_2$-Ap and $SiO_2$-Ap-ALN particles.
Figure 4:
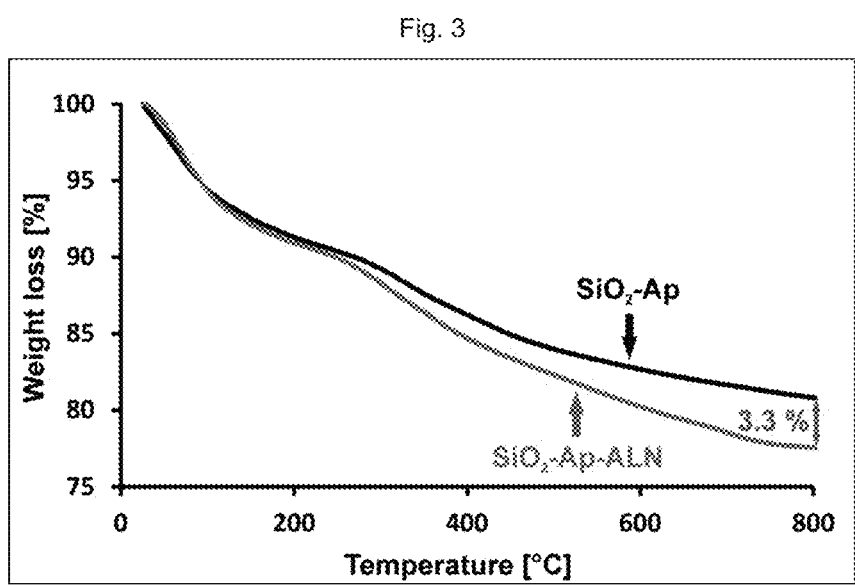
FIG. 4 summarizes the thermogravimetric profiles of $SiO_2$-Ap and $SiO_2$-Ap-ALN particles.

The results of the X-ray diffraction analysis (XRD) (FIG. 2) unambiguously confirmed the presence of the crystalline phase in the obtained material. Moreover, the signals appearing on the diffractograms at $2\theta$ equal to: 25.9; 32.0; 39.4; 42.2; 46.8; 53.2 are in agreement with literature values of signals attributed to hydroxyapatite.

The results of the studies confirmed the effectiveness of the proposed methodology for obtaining bioactive hybrid material ($SiO_2$-Ap) under mild conditions simulating the biomineralization process. Moreover, stability of the obtained material is based on interactions resulting from the strong affinity of ALN for apatite. The deprotonated oxygen atoms of the phosphate groups in ALN interact electrostatically with the calcium ions present on the surface of apatite. The resulting Ap-ALN conjugate does not affect the apatite crystal structure.

The obtained submicron $SiO_2$-Ap-ALN particles, as described in Example 2, were characterized by a number of complementary physicochemical methods (SEM, XPS, XRD, TG) (FIGS. 1-4). The XPS (FIG. 3) and TG (FIG. 4) analysis confirmed the efficiency of binding alendronate to the $SiO_2$-Ap bioactive carrier. Changes in the elemental composition of the surface of the obtained $SiO_2$-Ap-ALN material were demonstrated (XPS analysis, Table 2), as well as differences in the thermogravimetric profile (for the material with the drug attached, a weight loss greater by 3.3% in relation to the $SiO_2$-Ap carrier alone was found.). The obtained diffractogram for the material with the attached drug (FIG. 2) did not show significant differences compared to the diffraction pattern obtained for the carrier itself, which confirms that the process of ALN to $SiO_2$-Ap conjugation did not affect its crystal structure.

TABLE 2

| Results of XPS analysis | | | | | |
| --- | --- | --- | --- | --- | --- |
| Elemental composition (%) of the studied materials | O 1s | Si 2p | C 1s | N 1s | Ca 2p | P 2p |
| $SiO_2$—Ap | 62 | 3 | 4 | 1 | 26 | 4 |
| $SiO_2$—Ap—ALN | 60 | 3 | 8 | 2 | 23 | 4 |

Example 4. Preparation of the Chemically Cross-Linked Hydrogel Hybrid Materials with Dispersed Bioactive Mineral Phase Carrying Alendronate ($SiO_2$-Ap-ALN)

The submicron $SiO_2$-Ap-ALN particles obtained in the Example 2 were suspended in a biopolymer sol consisting of collagen, chitosan and lysine-functionalized hyaluronic acid, and cross-linked with genipin to obtain a hybrid material. For this purpose, three batches of the submicron bioactive mineral particles carrying sodium alendronate ($SiO_2$-Ap-ALN) were prepared, 5 mg, 2.5 mg, 1 mg, respectively, and each was suspended in 0.1 mL of water. Then, appropriate volumes of biopolymer solutions were added: 76 μl of chitosan (Ch) solution (1% by weight solution in 1% acetic acid), 540 μl of collagen (Col) solution (solution in hydrochloric acid with a concentration of 3.5 mg/mL—solution provided by the manufacturer BD Biosciences), 114 μl of solution of the lysine-modified hyaluronic acid ($HA_{mod}$) (1% by weight solution in 10×phosphate buffer (PBS); composed of: NaCl (c=1.37 M), KCl (c=27 mM), $Na_2HPO_4$ (c=43 mM), $KH_2PO_4$ (c=14 mM), pH adjusted to 7.4 with concentrated (c=35%) hydrochloric acid HCl solution). The obtained sol was shaken vigorously and then 170

μl of genipin solution (20 mM solution, prepared in 10×PBS) was added and incubated at 37° C. until complete cross-linking occurred. The obtained material was in the form of a hydrogel. The weight ratio of biopolymers in the obtained material was: Col:Ch:HA$_{mod}$—50:20:30.

Three concentrations of SiO$_2$-Ap-ALN particles suspended in the sol were tested. Using three different concentrations of suspensions/dispersions of the bioactive mineral particles (C1=5 mg/mL, C2=2.5 mg/mL, C3=1 mg/mL), three types of hybrid materials were obtained: ColChHA$_{mod}$ C1, ColChHA$_{mod}$ C2 and ColChHA$_{mod}$ C3. A hydrogel with an analogous biopolymer composition, but without the addition of the SiO$_2$-Ap-ALN particles (0.1 ml of water was added) was obtained as a control material (ColChHA$_{mod}$).

The procedure for preparation of the lysine-modified hyaluronic acid was presented in the publication (Gilarska, A et al., (2020), Int. J. Biol. Macromol, 155, 938-950).

In the first step, the MES buffer (50 mM) was prepared. For this purpose, 0.97 g of 2-(N-morpholino)ethanesulfonic acid (MES) was dissolved in 100 ml of deionized water and the pH was adjusted to 4 with 0.1 M NaOH solution. The whole mixture was filtered through a syringe filter. 500 mg of hyaluronic acid (HA) was dissolved in 20 mL of the MES buffer (50 mM, pH=4) and then 0.73 g of lysine, 360 mg of EDC (N-(3-dimethylaminopropyl)-N'-ethylcarbodiimide hydrochloride) and 220 mg of NHS (N-hydroxysuccinimide) was sequentially added (each of these reagents was first dissolved in 5 mL of MES buffer due to the gel consistency of the mixture). The mixture was stirred for 24 hours on a magnetic stirrer at room temperature, and then dialyzed overnight into 0.1 M aqueous Na$_2$CO$_3$ solution (lasting about 12 hours), followed by an 8-day dialysis against water. In the next step, the mixture was concentrated on evaporator (to a volume of about 50 mL) and freeze-dried for three days. The degree of lysine substitution of the product thus obtained (HA$_{mod}$) was determined by elemental analysis and $^1$H NMR spectroscopy, it came to about 25%.

Example 5. Characterization of the Chemically Cross-Linked Hydrogel Hybrid Materials with Dispersed Bioactive Mineral Phase Carrying Alendronate (SiO$_2$-Ap-ALN).

The obtained hydrogel hybrid materials, ColChHA$_{mod}$ C1, ColChHA$_{mod}$ C2, ColChHA$_{mod}$ C3, respectively, were subjected to physicochemical characteristics. The morphology, lyophilicity, swelling degree, and rheological properties were determined.

Figure 5:
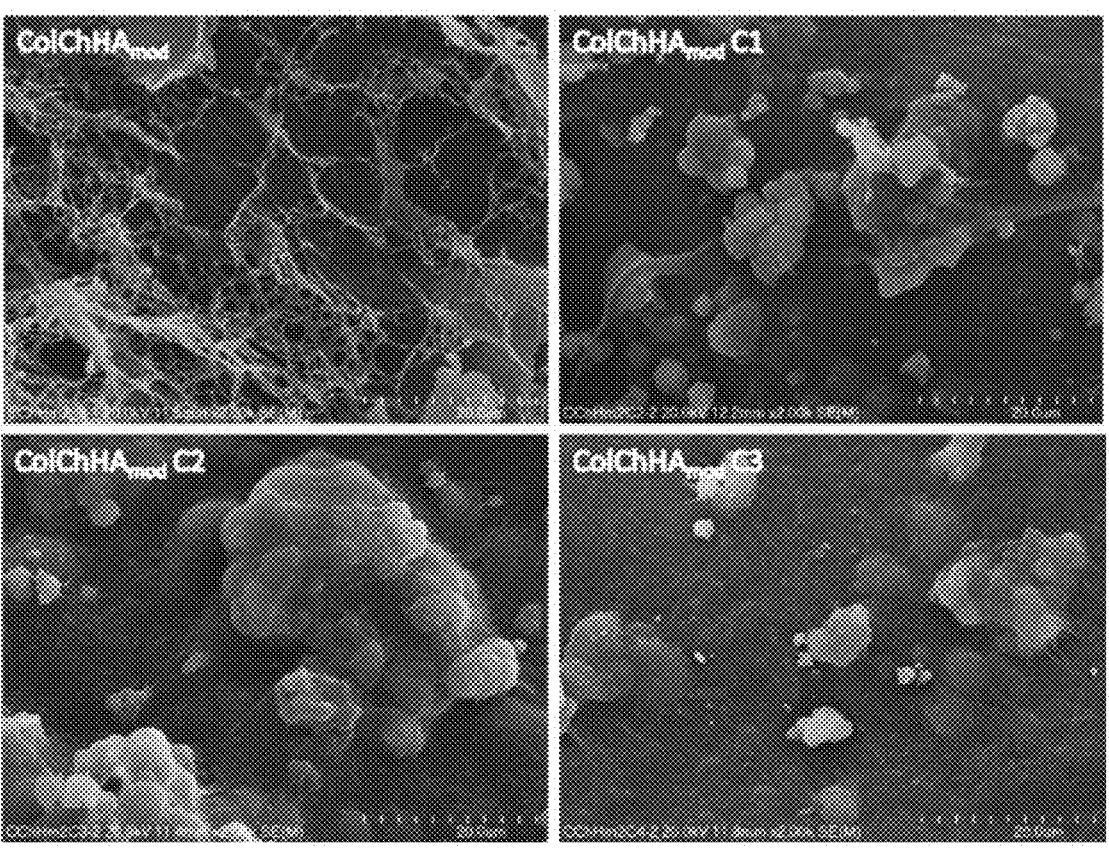
FIG. 5 shows SEM microphotographs demonstrating morphology of the obtained hybrid materials as well as the $ColChHA_{mod}$ control material.

Using the SEM technique, the microstructure of the obtained hybrid materials as well as the control material ColChHA$_{mod}$ was characterized. Analysis of the obtained microphotographs (FIG. 5) revealed the presence of the submicron SiO$_2$-Ap-ALN particles in each of the obtained hybrid systems. The particles existed both as individual objects as well as in the form of aggregates partially covered with the created biopolymer network.

Figure 6:
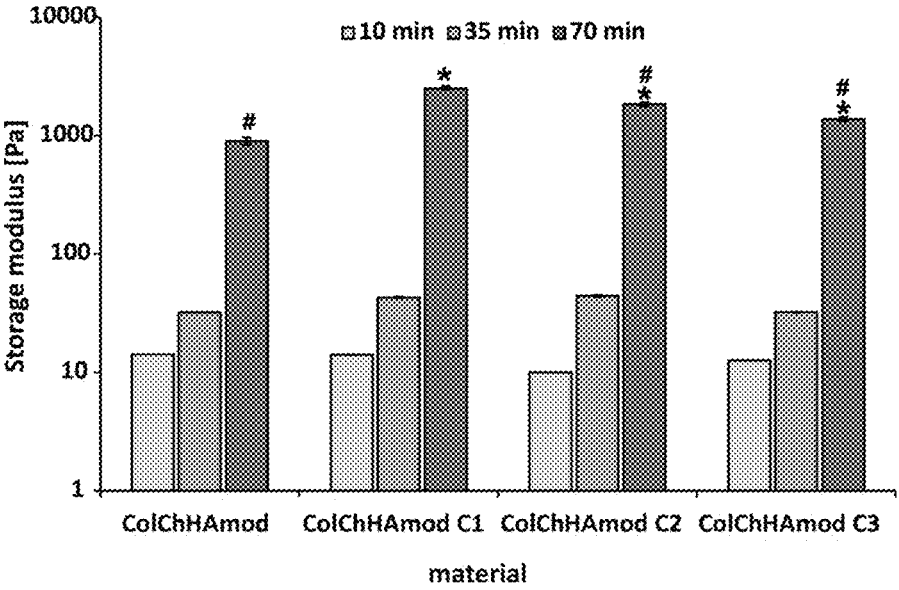
FIG. 6 summarizes results of the rheological studies, the G' values measured after 10, 35 and 70 minutes of the experiment, where the results are presented on a logarithmic scale. Statistical significance ($p < 0.05$) was demonstrated using the Student's test. * indicates statistical significance relative to the KolChHA$_{mod}$ results at 70 min, # indicates statistical significance relative to the KolChHA$_{mod}$ C1 results after 70 min.

In order to confirm the possibility of using the developed systems as injectable materials, rheological measurements were carried out in the oscillatory mode. Elastic modulus (G') values measured after 10, 35 and 70 minutes of the experiment are shown in FIG. 6 (the experiment was carried out at 37° C., after adding genipin solution to the sol as described above). By tracking the changes of the elastic modulus (G') over time, it was possible to verify the transition from the sol to gel state and thus to demonstrate the injectable potential of the obtained materials. At the beginning of the gelling process (10 minutes after preparing the mixture), the values of the elastic modulus for all materials were at a low level (in the range of 10-14 Pa), confirming their viscoelastic state and the injectable form. The G' values increased significantly after 35 minutes, reaching a maximum value within 70 minutes from the start of the cross-linking process (gel formation). Thus, a comparison of the G' value at the beginning and the end of the rheological experiment proved that the developed materials can function as injectable materials.

Moreover, the obtained results demonstrated that introduction of the bioactive carrier into the biopolymer matrix significantly improved mechanical properties of the obtained hybrids. A statistically significant difference was demonstrated for the G' value after 70 min of gelation for all hybrid materials, in comparison with the elasticity modulus (G' after 70 min) obtained for the control material. An increase in the value of the elasticity modulus (G') from the value of 900 Pa for the polymer matrix, to 2500 Pa for the system with the highest carrier content (ColChHA$_{mod}$ C1) after 70 min of the gelling process was also observed (FIG. 6) (statistical significance in relation to all the materials).

The above results clearly prove that after the end of the gelation process (after 70 min) the hybrid materials, while maintaining the injectability typical for the polymer matrix itself, are characterized by significantly higher (statistical significance) values of the elastic modulus.

Figure 7:
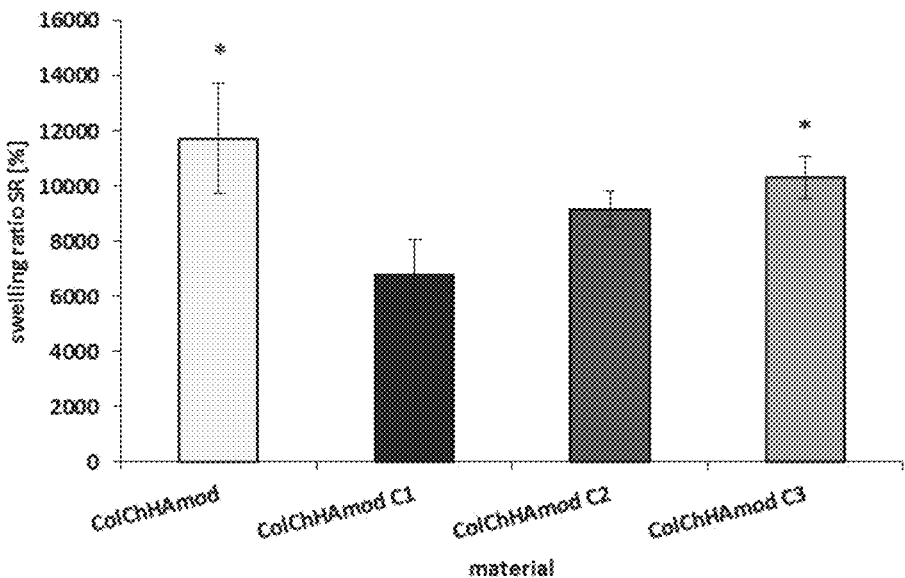
FIG. 7 summarizes the results of the swelling degree tests.

The degree of swelling (SP) was also determined for the obtained hybrid materials. The experiment was carried out under physiological conditions (pH=7.4; temp=37° C.), the results are shown in FIG. 7. Analyzing the obtained results, it can be seen that all tested materials show the swelling capacity (SP in the range of 6700-11700%), while the presence of SiO$_2$-Ap-ALN particles has a significant impact on the swelling properties of the hybrid systems. The performed swelling tests showed that with increasing concentration of SiO$_2$-Ap-ALN particles, the degree of swelling decreased (FIG. 7). Therefore, this result indicates that the obtained particles affect the stiffness of the hydrogel structure, which was also confirmed by rheological tests.

The lyophilicity of the surfaces of the obtained materials was also examined. The results obtained on the basis of the measurements of contact angles are summarized in Table 3. Analyzing the obtained data, it can be noticed that introduction of SiO$_2$-Ap-ALN particles into the biopolymer matrix causes the surface of the hybrid materials to become more hydrophilic, as evidenced by lower values of contact angles, as compared with the control material (ColChHA$_{mod}$). It was observed that the material with the highest concentration of the particles (ColChHA$_{mod}$ C1) had the most hydrophilic surface (66°). The improvement in hydrophilicity can be explained by the presence of SiO$_2$-Ap-ALN hybrid particles on the surface of the materials (SEM micrographs presented in FIG. 5) containing surface-exposed hydrophilic amine groups derived from the attached alendronate (as confirmed by XPS analysis).

TABLE 3

| Values of contact angles for the obtained materials | |
|---|---|
| Material type | Contact angle value [°] |
| ColChHA$_{mod}$ | 77.7 ± 1.3 |
| ColChHA$_{mod}$ C1 | 65.8 ± 0.6 |
| ColChHA$_{mod}$ C2 | 70.9 ± 1.3 |
| ColChHA$_{mod}$ C3 | 67.1 ± 0.8 |

Enzymatic Degradation

Figure 8:
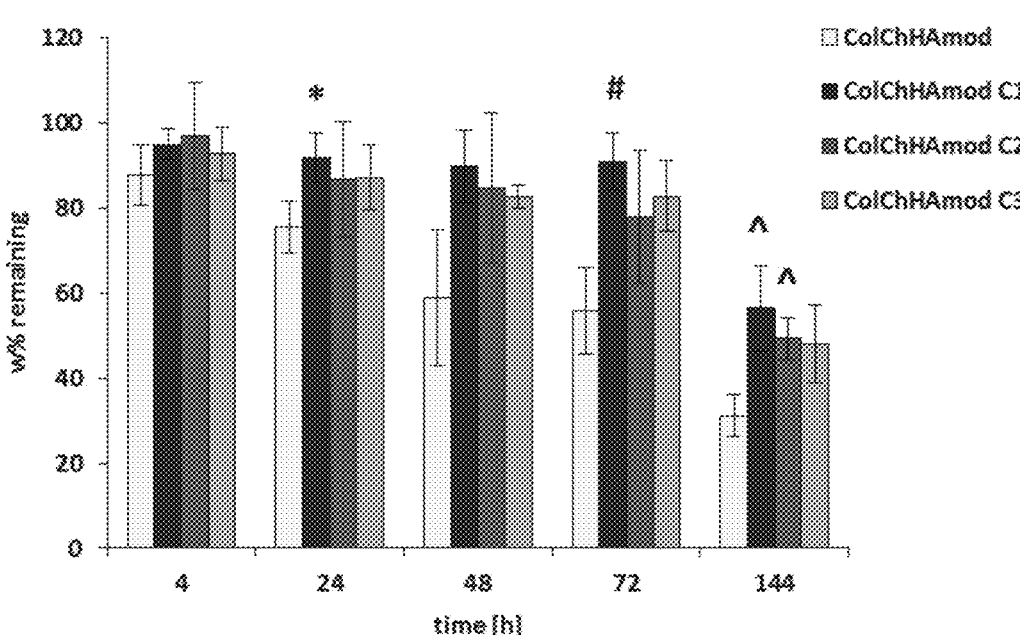
FIG. 8 summarizes the results of the enzymatic degradation studies.

The obtained materials were also subjected to the enzymatic degradation process in the presence of the enzyme—collagenase. The enzymatic degradation was studied for 144 hours. FIG. 8 shows changes in the mass of materials during incubation in a collagenase solution. A significant slowdown of the enzymatic degradation process was observed for all the materials with an introduced carrier. After 4 hours of enzymatic degradation, a slight weight loss was noted for the hybrid materials (about 3-7%) and 12% for the ColChHA$_{mod}$ material. At subsequent measurement points, significant changes in the remaining weight of the control material were observed (31% after 144 h), while the weight loss for the hybrid materials went off much slower. After 144 h of degradation of the hybrid materials, weight loss of about 44-52% was observed. When analyzing the weight loss of all the tested materials at a given point of the experiment, a tendency can be indicated that with an increase in the content of SiO$_2$-Ap-ALN particles, the speed of the degradation process decreases. These results are in line with the results of the rheological experiment, which confirmed the improvement of the mechanical properties of the hybrid materials along with the increasing concentration of SiO$_2$-Ap-ALN particles in the system.

Bioactive Properties

Figure 9:
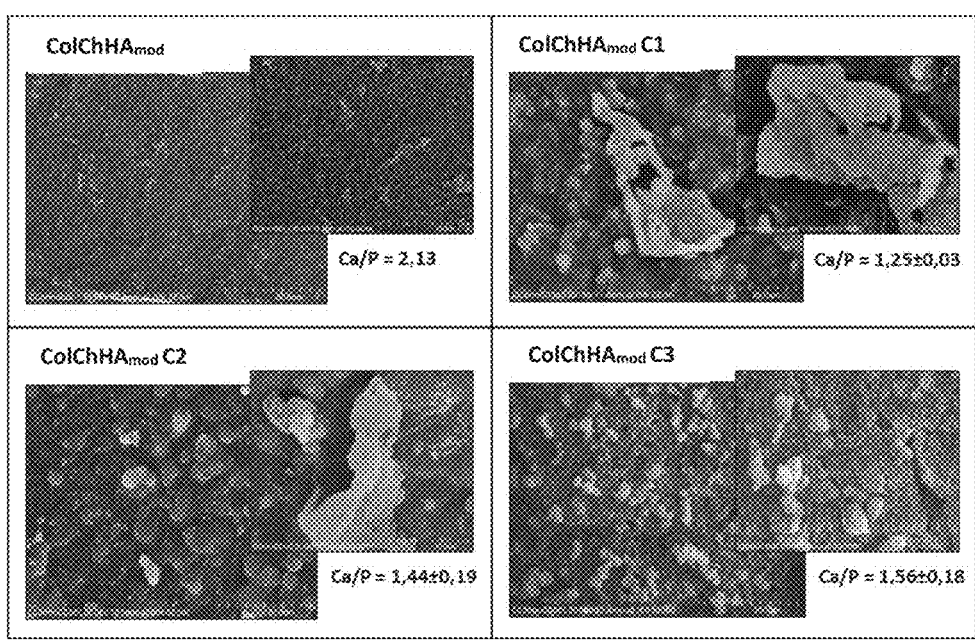
FIG. 9 shows SEM microphotographs of the hybrid materials together with the values of calcium to phosphorus ratio (Ca/P), as determined by EDS for the mineral phase formed on the surface of the materials after 3 days of incubation in SBF.

In order to demonstrate that the obtained hybrid materials, thanks to the presence of silica-apatite particles, will favor the bio-integration of the material with the bone and thus support the bone mineralization process disturbed in the process of osteoporosis, their bioactive properties were examined. An in vitro biomineralization experiment was carried out under conditions of simulated body fluid (SBF). Literature data show that materials showing the ability to produce an apatite layer on their surface under SBF conditions will also undergo biomineralization in a living organism, thus ensuring effective integration of the scaffold with natural bone. The biomineralization experiment under model conditions included a 5-day incubation of the materials in SBF at 37° C. Subsequently, the materials were tested using SEM and EDS techniques. FIG. 9 shows the obtained SEM microphotographs and the values of the calcium to phosphorus ratio (Ca/P) determined by the EDS technique for the mineral phase formed on the surface of the materials after 3 days of incubation in SBF.

Detailed analysis of the results (SEM/EDS) allowed to state that the formation of the mineral phase in the form of a flower structure, in which the Ca/P ratio is characteristic of apatite, was observed for the hybrid materials ColChHA$_{mod}$ C1 and ColChHA$_{mod}$ C2, after 3 days. In addition, due to the fact that the hydrogel matrix according to the present invention consists of 30% by weight of the modified hyaluronic acid, additional support for biomineralization from hyaluronic acid was observed (formation of the mineral phase in the form of layers on the surface of ColCh-HA$_{mod}$ and ColChHA$_{mod}$ C3). In case of the previous invention, the polymer matrix with 10 wt. % of unmodified hyaluronic acid did not exhibit this property. It is worth noting that the material presented in the previous application was subjected to a similar experiment (bioactivity study in SBF); in that case, the process of biomineralization took place only after 7 days.

The obtained results clearly indicate that the discussed hybrid materials with the SiO$_2$-Ap-ALN particles in concentration in the range of 1-5 mg/ml are characterized by bioactive properties ensuring a significant acceleration of biomineralization process, namely up to 3 days, and thus by more effective biointegration of the material with natural bone.

Studies of the Biological Properties of the Hybrid Material

The obtained hydrogel-based hybrid materials were also subjected to preliminary biological tests in vitro with the use of MG-63 osteoblastic cells. Proliferation, alkaline phosphatase activity, morphology and adhesions of cells grown on the surface of the tested materials were determined. The performed biological tests in vitro demonstrated that introduction of SiO$_2$-Ap-ALN particles at the tested concentrations of C1, C2 and C3 into the hydrogel matrix did not deteriorate the biocompatibility of hybrid materials compared to the control material ColChHA$_{mod}$. The results of the cell viability tests (the Alamar Blue test was used) carried out at the 1st, 3rd and 7th day of culture (FIG. 10A) showed that all the obtained hybrid materials supported the proliferation capacity of MG-63 cells. A similar (without statistically significant differences) increase in the number of cells was observed in the consecutive days (1, 3, 7) of the experiment performed with the use of hybrid materials containing the SiO$_2$-Ap-ALN particles in C1 and C2 concentrations, as compared to the results for the control (ColChHA$_{mod}$).

Figure 10:
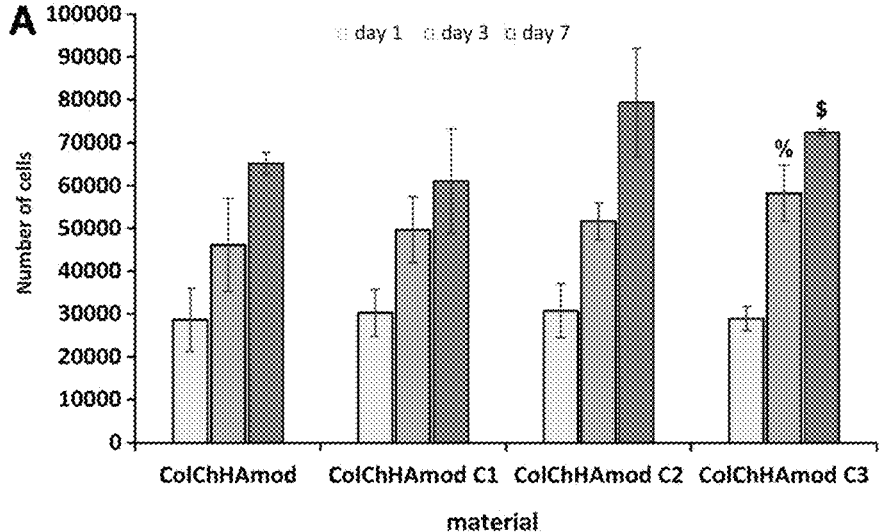
FIG. 10 shows (A) the results of the Alamar Blue test on the days 1, 3 and 7 of growing the MG-63 cells on the tested materials. (B) Alkaline phosphatase activity after 3 and 7 days of growing the MG-63 cells on the tested materials. Statistical significance (p<0.05) was demonstrated using the Student's test. (A) % indicates statistical significance relative to the result for ColChHAmod day 3, $ indicates statistical significance relative to the result for the ColChHAmod day 7 (B) * indicates statistical significance relative to the result for the control day 3, ** indicates statistical significance relative to the result for the control day 7, # indicates statistical significance relative to the result for ColChHAmod C1 day 3. Cells grown in the culture dish were used as controls.
Figure 10:
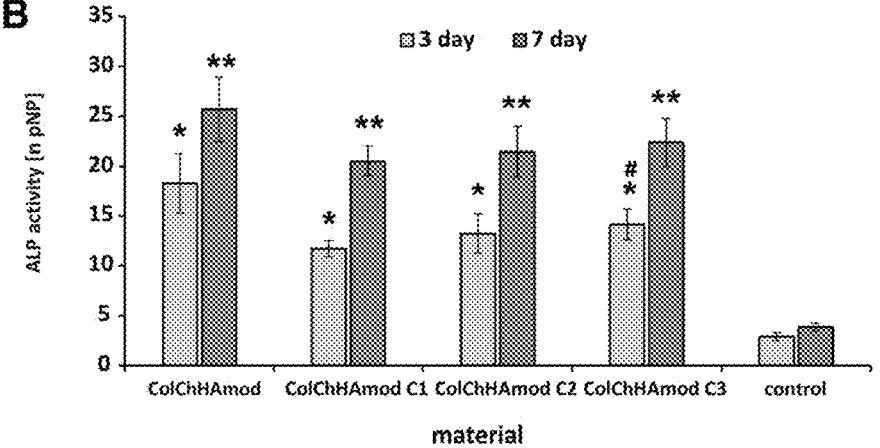

Activity of the alkaline phosphatase (ALP) as a marker confirming the phenotype and mineralization of osteoblasts on the 3rd and 7th day of culturing was also tested (FIG. 10B). For all the analyzed materials, an increase in activity was observed after 7 days of the experiment. The level of ALP on both the third and the seventh day of culture was significantly higher compared to the ALP activity of the cells on the culture plate. When analyzing the effect of SiO$_2$-Ap-ALN particles concentration on ALP activity, statistically significant differences were observed only for ColCh-HAmod C3 material on the 3rd day of the experiment (against ColChHA$_{mod}$ C1 on the 3rd day). On day 7 of culturing, no significant differences in ALP activity between the obtained hybrid systems were found.

Figure 11:
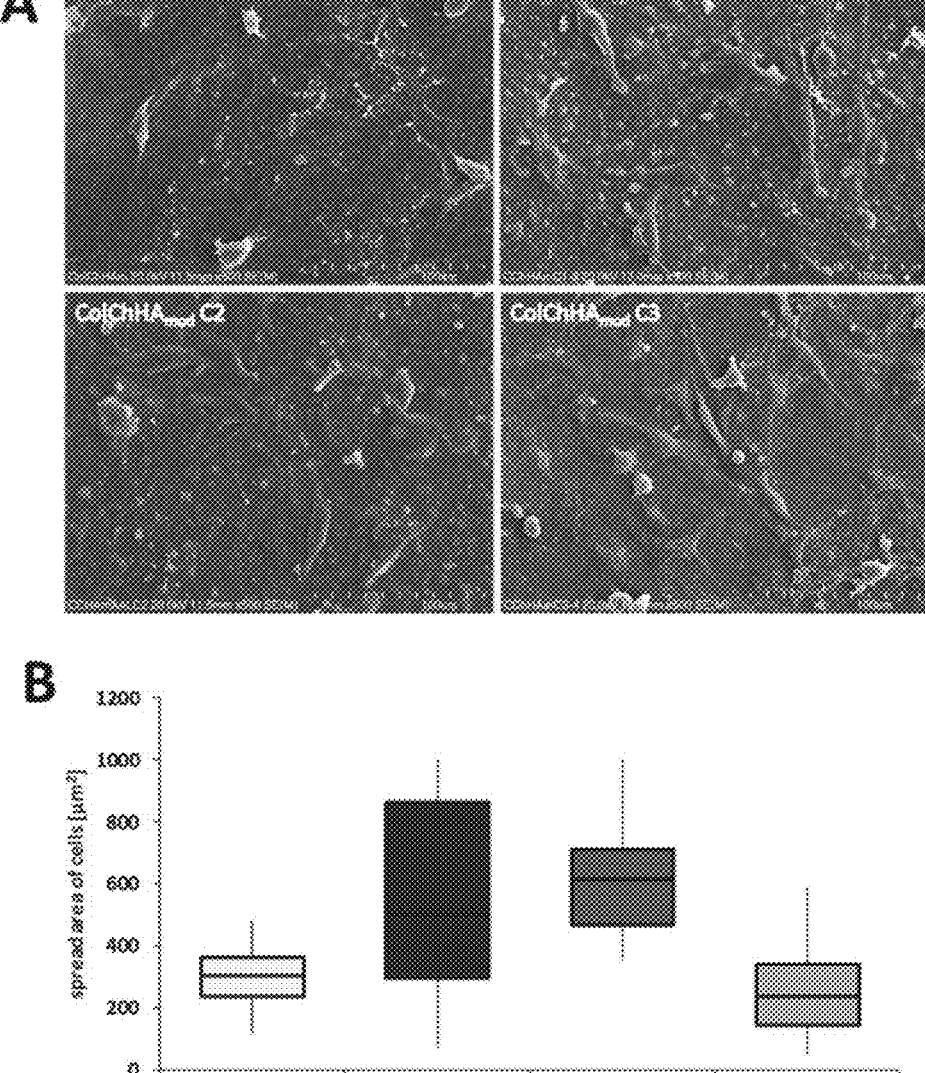
FIG. 11 shows (A) a summary of SEM microphotographs showing the morphology of the fixed MG-63 cells after 3 days of growing on the surface of the tested materials (B) a graph showing the surface distribution of the MG-63 cells after 3 days of growing (estimated based on the obtained SEM microphotographs).

The morphology and adhesion of MG-63 cells after 3 days of culture on the surface of the materials were also analyzed. Cells were fixed and imaged using the SEM technique. FIG. 11 summarizes the SEM microphotographs showing morphology of the fixed cells (FIG. 11A) as well as a plot of the MG-63 cell surface distribution after 3 days of growing (estimated based on the obtained SEM microphotographs) (FIG. 11B). While analyzing the obtained microphotographs (FIG. 11A), it can be concluded that the cells adhere equally well to the surface of the hybrid materials and to the surface of the control hydrogel (ColChHA$_{mod}$). The estimated cell surface distribution (FIG. 11B) shows that cells grown on the ColChHA$_{mod}$ control material and in the hybrid system with the lowest concentration of the SiO$_2$-Ap-ALN (C3) particles occupy a comparable surface area and have a similar morphology. The morphology of cells grown on the hybrid materials with C1 and C2 particle concentration is more diverse. A population of flattened, occupying larger area cells with elongated shapes was observed. Therefore, the data demonstrate that the presence of SiO$_2$-Ap-ALN particles has a positive effect on cell adhesion.

Study of the Therapeutic Properties

In order to demonstrate the ability of the developed hybrid material to inhibit bone resorption, preliminary biological studies were carried out in vitro using a model osteoclast line (J774A.1 cells). This line constitutes the reference line used in in vitro analyzes of metabolism of compounds belonging to the bisphosphonate group.

Figure 12:
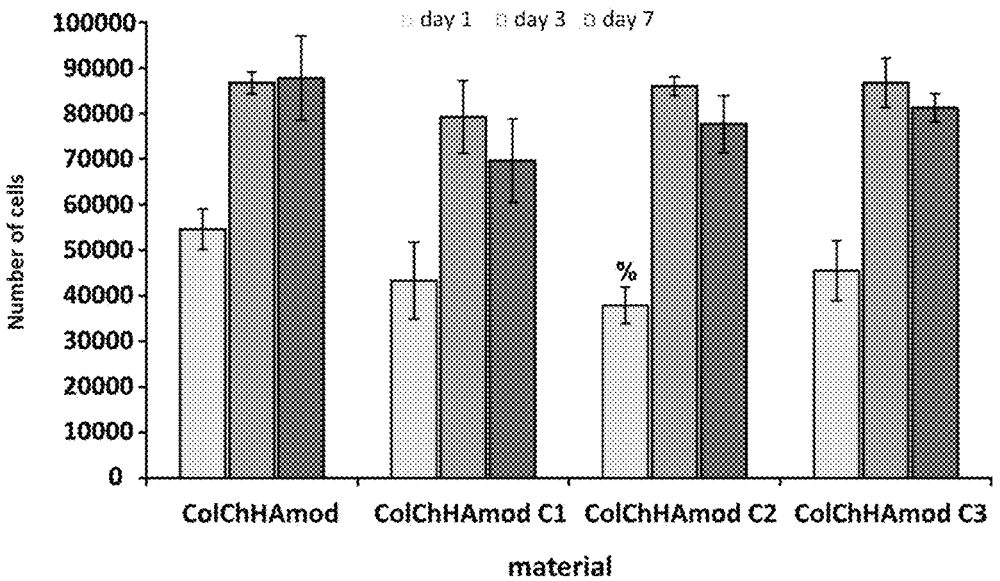
FIG. 12 shows the results of the Alamar Blue assay after 1, 3 and 7 days of growing of the J774A.1 cells on the tested materials. Statistical significance (p<0.05) was demonstrated using the Student's test. The % indicates statistical significance relative to results for ColChHAmod day 1.
Figure 13:
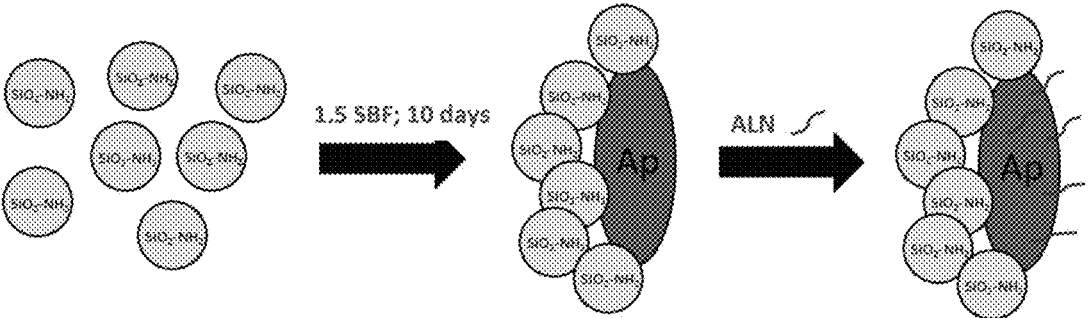
FIG. 13 shows a scheme of formation of the SiO$_2$-Ap-ALN particles (SiO$_2$—NH$_2$-amine functionalized silica particles; Ap—apatite layer formed on the surface of silica particles after incubation in 1.5 M SBF; ALN—sodium alendronate).
Figure 14:
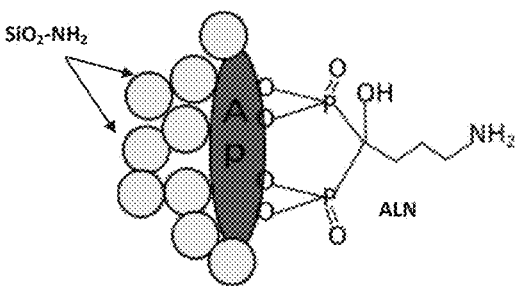
FIG. 14 shows a pattern of the obtained SiO$_2$-Ap-ALN particles (SiO$_2$—NH$_2$-amino functional silica particles; Ap—apatite layer; ALN—sodium alendronate). The obtained product (SiO$_2$-Ap-ALN) was suspended in a biopolymer sol (collagen-chitosan-hyaluronic) and cross-linked with genipin to obtain the hybrid material useful as the material for filling osteoporotic defects.
Figure 15:
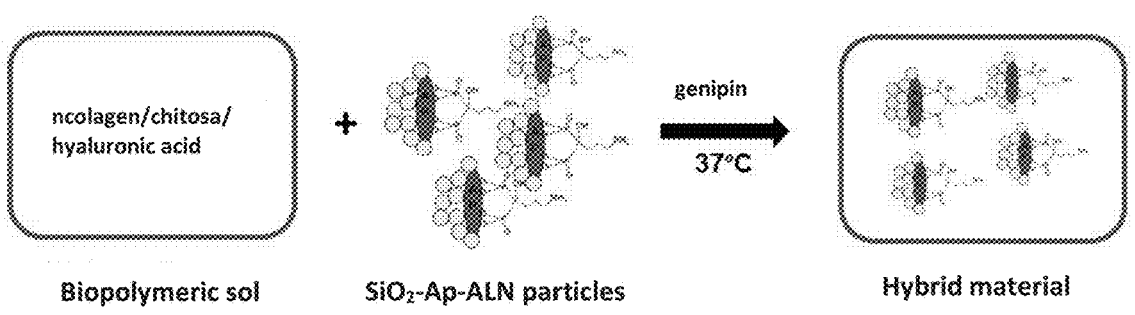
FIG. 15 shows a schematic view of formation of the hybrid material.

The results of cell viability tests (the Alamar Blue test was used) performed after 1, 3 and 7 days of cell growing are shown in FIG. 12. The preliminary biological studies showed that proliferation of osteoclastic cells grown on hybrid materials was inhibited after 7 days of the experiment. A tendency to increase this effect with the increase in concentration of $SiO_2$-Ap-ALN particles present in the hydrogel matrix was observed, and was most visible for the $ColChHA_{mod}$ C1 system. Thus, it was shown that the tested hybrid materials with the proposed content of the $SiO_2$-Ap-ALN particles (C1, C2 and C3) have a therapeutic potential manifested by impairment of the activity of the model osteoclastic cells. Therefore, taking into account the form of the developed formulation and the possibility of its local administration by injection directly into the less, it will be possible to ensure the local action of the drug, thus minimizing the systemic side effects of application of alendronate. The material presented in the scope of the previous application had no therapeutic properties.

Example 6. Biological Evaluation In Vivo

Considering the potential applications of the developed materials biological evaluation in vivo was performed. Based on the results of physicochemical characterization as well as in vitro biological studies, the hybrid with the highest $SiO_2$-Ap-ALN concentration (ColChHAmod C1) and pristine ColChHAmod hydrogel as a control were selected for further biological research. The experiments on the mouse model was performed to evaluate the biocompatibility of the selected systems and examine the potential and safety of obtained materials in in vivo conditions. The injectability as well as the ability to gel in vivo was verified while the panel of biochemical and histopathological analyses enabled the determination of hemo-, hepato-or nephrotoxicity of developed systems.

Hydrogel-Based Hybrid Materials Injectability and Degradation In Vivo

Figure 16:
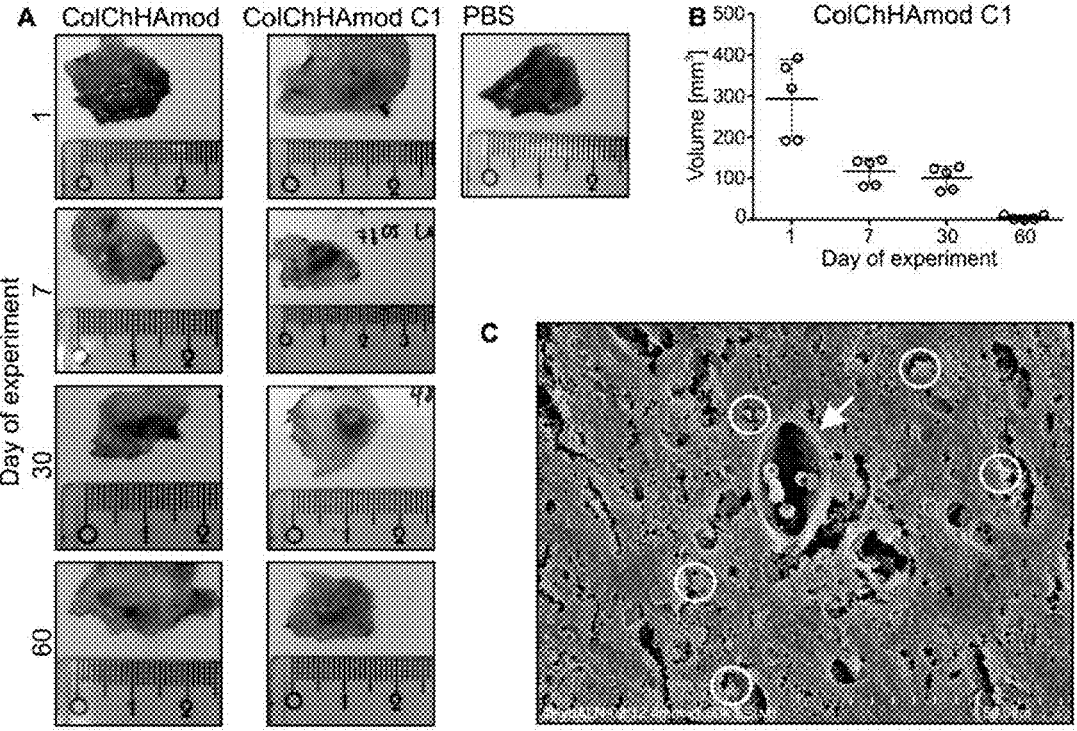
FIG. 16 shows: (A) fragments of isolated skin with hydrogel-based materials, (B) a decrease in hydrogel volume observed after various periods followed material injection, (C) representative SEM images of ColChHAmodC1 isolated from mice skin after 60 days post injection. White circle indicate hydroxyapatite aggregates as determined by EDS analysis. White arrow points out blood vessel in hydrogel.

In in vivo studies, the tested materials were injected subcutaneously (right flank, shoulder area) into the healthy C57Bl/6 mice. Before administration, all components were mixed, transferred into a syringe, and incubated for 15 minutes at 37° C. (to induce gel formation). After incubation, the color of the tested materials was light grey to blue-green; all the materials continued to be liquid; hence no problems were encountered with their subcutaneous administration. Moreover, no hydrogel leakage was observed immediately after administration (through the hole created when the needle was removed) thus, and the entire mixture was injected. It was therefore confirmed that all tested materials had very good injectability. Mice were sacrificed at $1^{st}$, $7^{th}$, $30^{th}$, $60^{th}$ day of the experiment, and both ColChHAmod and ColChHAmod C1 visualized after skin removal (FIG. 16A). The color of both tested materials was blue. ColChHAmod was softer, more hydrated, and had a decidedly less compact structure than ColChHAmod C1. The progress of volume change quantitively over time only for ColChHAmod C1 was observed. A significant, rapid decrease in ColChHAmod C1 volume was revealed after seven days (volume was 2.5 times smaller than this observed after one-day post-injection), indicating their biodegradation (FIG. 16B). Between 7 and 30 days of the experiment, the volume of ColChHAmod C1 did not change significantly, and finally, at the end of the experiment lasting 60 days, the volume was almost 60 times smaller than this observed after one day post-injection (FIG. 16). Also, ColChHAmod C1 had not gel's consistency anymore, and this material was hard, light blue-green in color, and blood vessels were observed near it. The significant postmortem degradation of ColChHAmod was also revealed. On the 60th day of the experiment, the material no longer resembled a gel; its debris/residues were visible under the skin as black fibers.

Biosafety In Vivo of ColChHAmod and ColChHAmod C1 Materials

Figure 17:
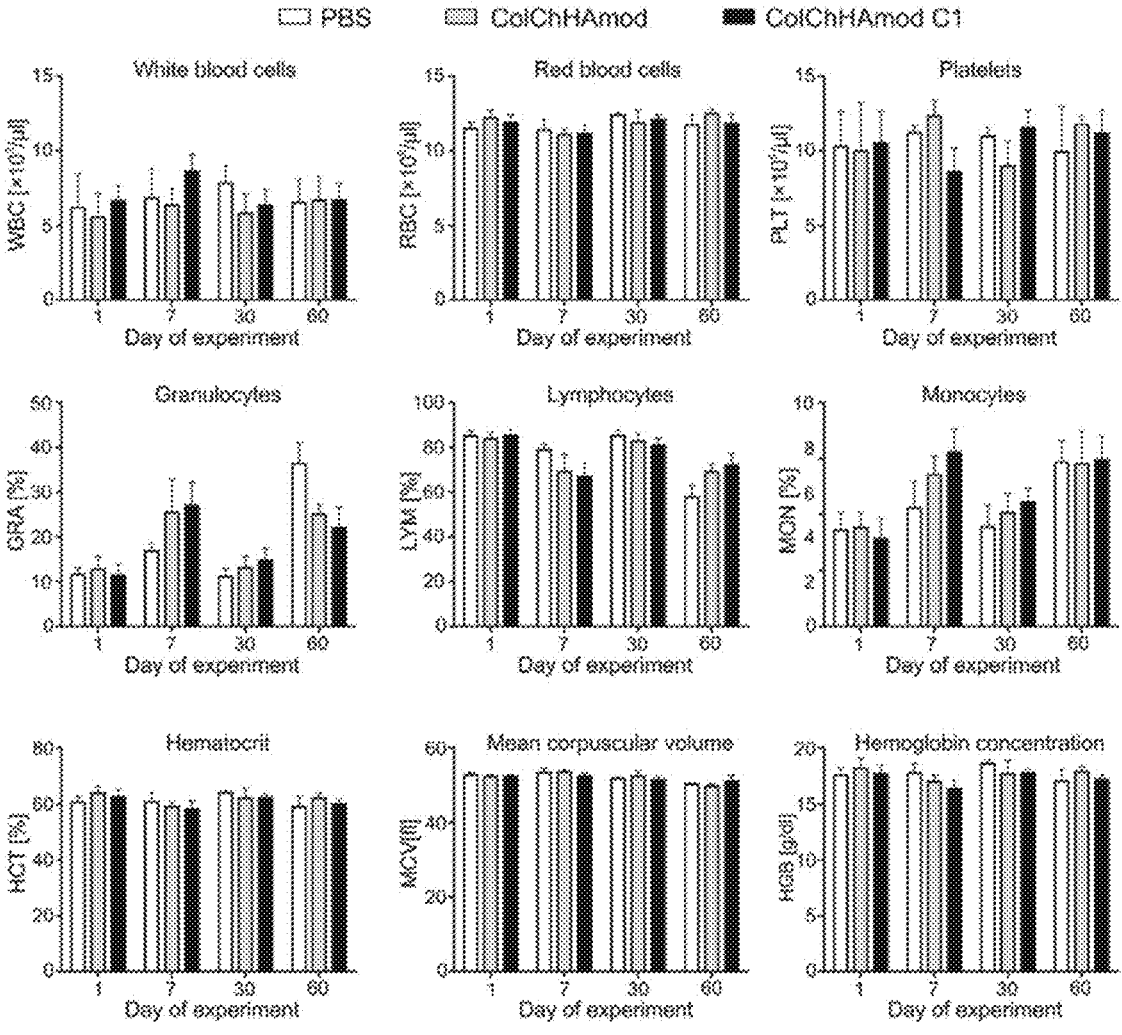
FIG. 17 shows blood hematology analyses performed for mice exposed to hydrogels.
Figure 18:
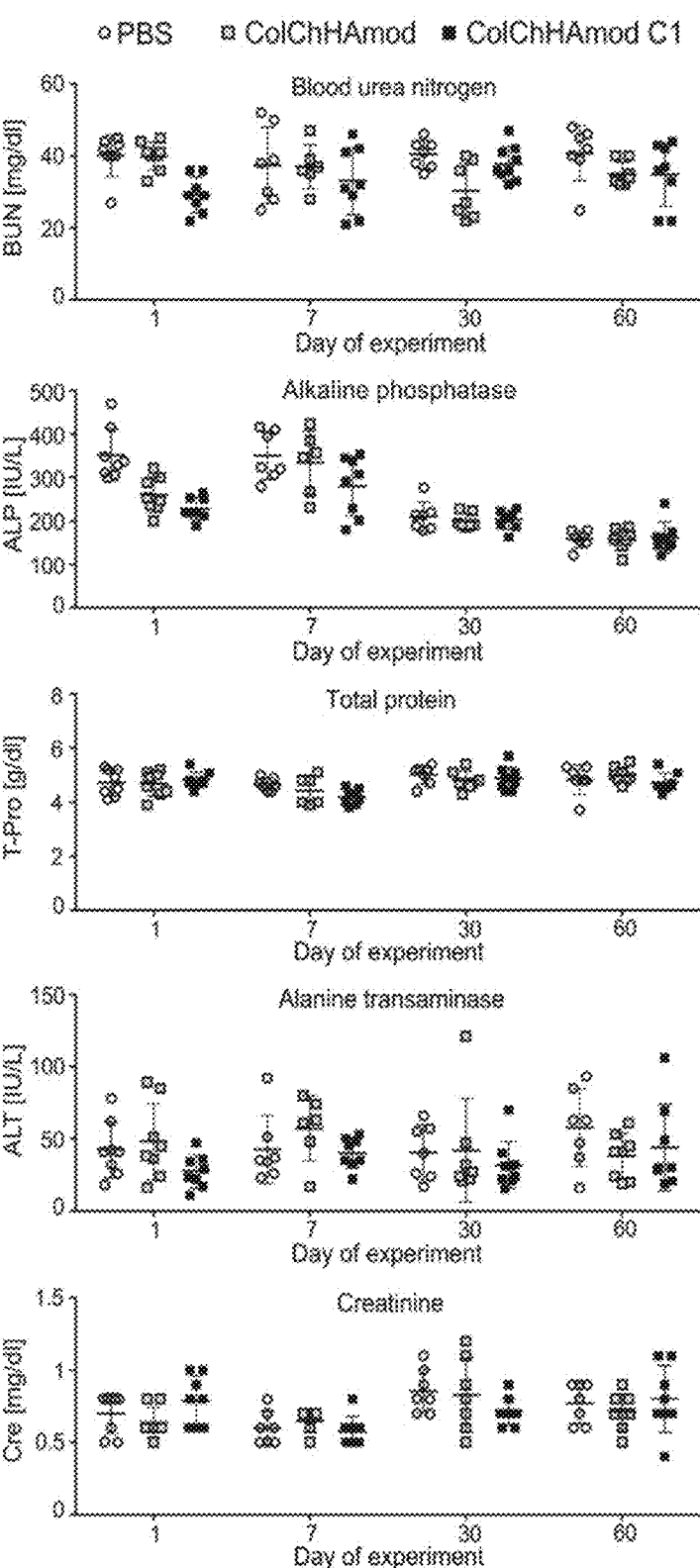
FIG. 18 shows biochemical serum analyses performed for mice exposed to hydrogels.

Analysis of systemic biocompatibility aimed to exclude adverse reactions provoked by subcutaneous administration of materials and products of their degradation. Although the materials have been injected subcutaneously, their degradation products may cause systemic toxicity by entering the bloodstream. The animals were euthanized at different times after administering the materials (1 day, 7 days, 30 days, 60 days), which allowed investigating the potential acute and chronic toxicity. No weight loss or disturbing changes in the animals' appearance and behavior were observed during the experiment. As shown in FIG. 17 and FIG. 18, no changes were observed in blood morphology or in the activity or concentration of hepatotoxicity (ALT, T-Pro), nephrotoxicity (BUN, Cre), or other tissue damage (ALP) markers.

Figure 19:
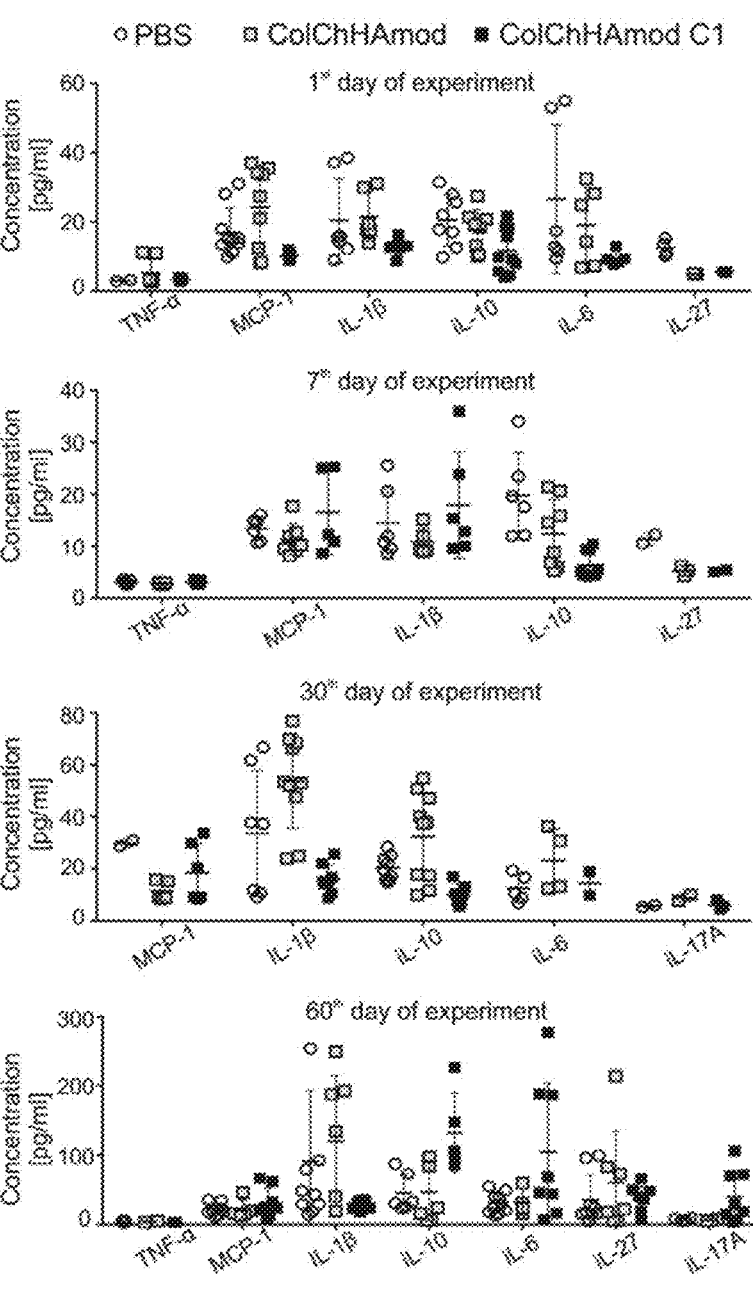
FIG. 19 shows cytokine detection in sera after materials administration.

Finally, serum concentrations of cytokines, including proinflammatory cytokines, confirmed the absence of subcutaneously administered hydrogels' or products of their degradation immunotoxicity (FIG. 19). These results indicate a lack of systemic toxicity that could result from administration to animals of hydrogel containing potentially toxic products of degradation.

They, therefore, confirm that the use of biomaterials loaded with $SiO_2$-Ap-ALN can be a promising method of repair of osteoporotic bone without the risk of systemic toxicity caused by the drug or other products of materials degradation.

Figure 20:
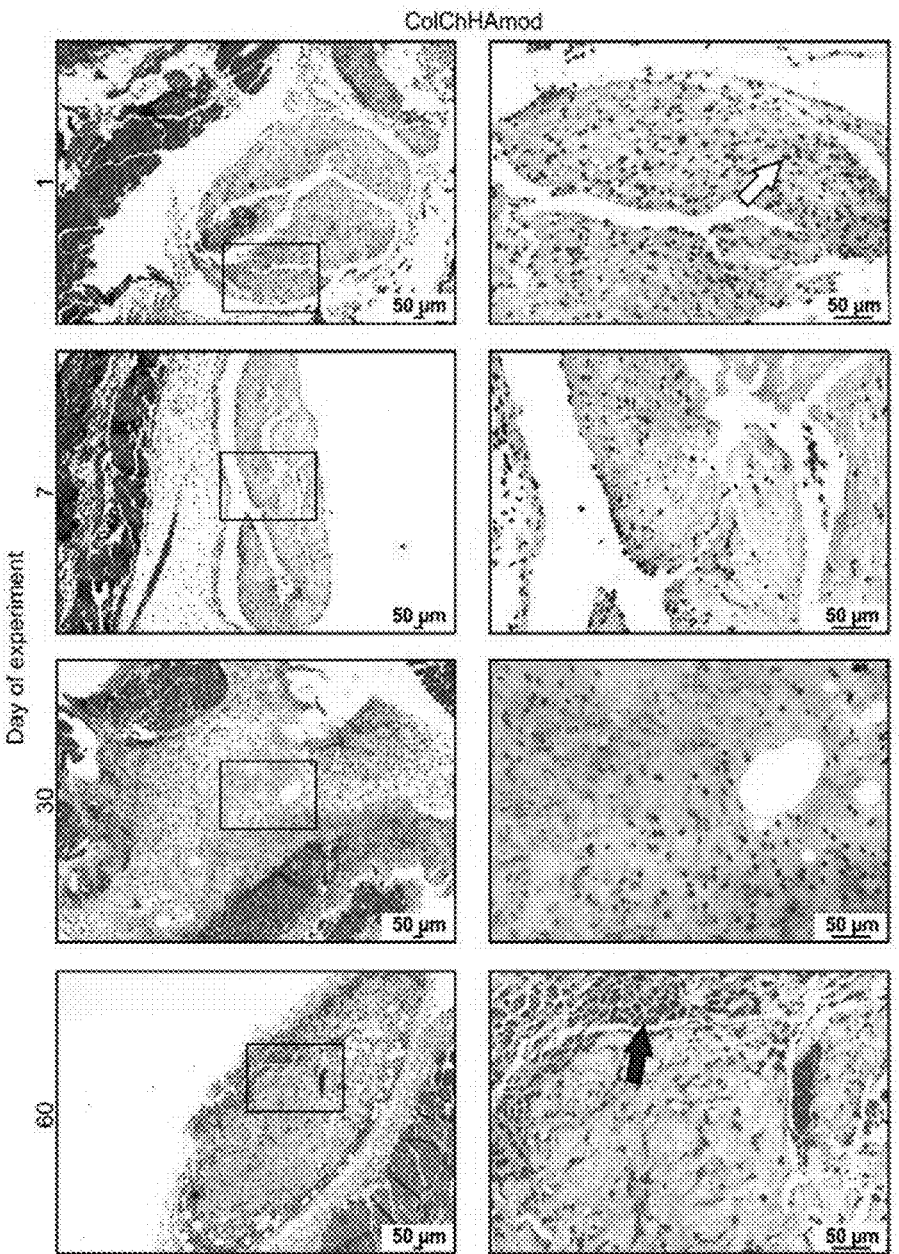
FIG. 20 shows hydrogel ColChHAmod stained with Masson's Trichrome. The white arrow indicates neutrophils and dark grey arrow indicates macrophages.
Figure 21:
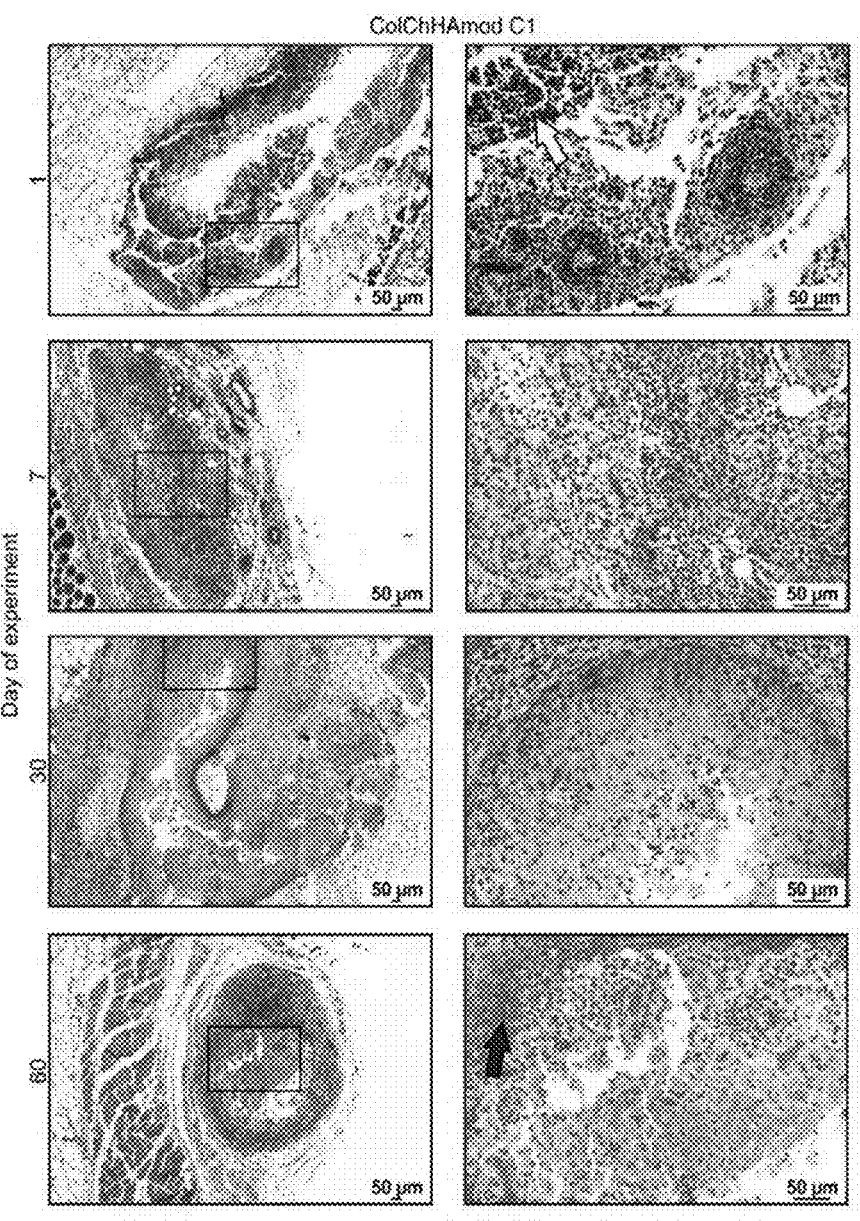
FIG. 21 shows hydrogel ColChHAmod C1 stained with Masson's Trichrome. The square is marked with an area that is shown at a larger magnification. The white arrow indicates neutrophils and dark grey arrow indicates macrophages.

Biological Changes Occurring Within the Hydrogels and Their Interaction with Cells In Vivo The changes in tested materials (isolated with skin fragments) at various times after their administration was also investigated. First of all, the recruitment of the host cells to the material was analysed. Twenty-four hours after the subcutaneous administration of ColChHAmod and ColChHAmod C1, an influx of immune cells (mainly neutrophils) responsible for developing local inflammation (FIG. 20 and FIG. 21) was observed. Immune cells were present in materials at all time points. However, the longer time after the biomaterials' administration, more leukocyte populations were recruited. Therefore, on the 7th day after administration, macrophages and lymphocytes were also visible in addition to neutrophils. The influx of immune cells occurs throughout the material volume; however, this phenomenon was much more intense at the periphery of materials. With ColChHAmod C1, a more intense inflammation was observed. The result was the production by fibroblasts of animal skin a clear layer of collagen (fibrotic capsule formation) around the hydrogel with $SiO_2$-Ap-ALN, visible on the 30th and 60th day after administering the material. This phenomenon was much less severe with ColChHAmod hydrogel. For ColChHAmod material, inhibition of the proinflammatory response was observed on the 60th day after administration. Moreover, the newly created blood vessels in isolated sections of materials 60 days after the administration was observed. The presence of blood vessels within the materials was also confirmed by SEM analysis (FIG. 16C).

Overall, the systemic proinflammatory response manifested by elevated proinflammatory cytokines in the blood (as it is demonstrated in FIG. 21) was not revealed. Thus, our results indicate that only local inflammation can be induced after administering the tested materials.

Based on the performed research, the following unexpected advantages of the obtained hybrid material can be indicated:

therapeutic potential—preliminary in vitro biological tests were performed using the osteoclast cell line (J774A.1 cells), and demonstrated that hybrid materials with the proposed composition and content of alendronate have therapeutic potential manifested by impairment of the activity of the model osteoclastic cells, improvement of bioactivity—accelerated biomineralization of the hydrogel material was observed. Detailed analysis of the results (SEM/EDS) allowed to state that in case of higher $SiO_2$-Ap-ALN (C1, C2) contents, after 3 days of incubation of the material in simulated body fluid (SBF), a new mineral phase is formed, ensuring faster biointegration of the material with natural bone, injectability of the hybrid materials characterized by very good mechanical properties. Therefore, taking into account the form of the developed formulation and the possibility of its local administration by injection into the loss, it will be possible to ensure the local action of alendronate, thus minimizing its systemic side effects related to oral or intravenous administration, biocompatibility—the performed in vitro biological tests have shown that the presence of the $SiO_2$-Ap-ALN particles does not reduce biocompatibility of the hybrid materials (compared to the $KolChHA_{mod}$ control material), as well as their ability to support adhesion, proliferation, and also to maintain the phenotype of osteoblastic cells (MG-63), the safety of developed materials in in vivo conditions. The results of in vivo experiments indicated a lack of systemic toxicity of developed systems and thus demonstrated that the use of hybrid with SiO2-Ap-ALN can be a promising method for repair of osteoporotic bone, lack of the systemic proinflammatory response—there was only local inflammation observed, the materials induced the angiogenesis—novel blood vessels were observed within the hybrid material after 60 days of in vivo experiment, the injectability of the materials and their ability to gel in vivo was confirmed.

The invention claimed is:

1. A method of producing a multifunctional hydrogel hybrid material which contains a biopolymer matrix containing collagen, chitosan, and lysine-modified hyaluronic acid, silica-apatite particles functionalized with amino groups, an active substance in the form of alendronate attached to silica-apatite particles, and genipin as a cross-linking substance, the method comprising the following steps:

a) functionalizing silica particles with amino groups, b) suspending the silica particles obtained in step a) in an aqueous SBF solution to obtain, after 10 days of incubation, silica-apatite particles, c) attaching sodium alendronate to the silica-apatite particles obtained in step b), d) adding a solution of the collagen, the chitosan and the lysine-modified hyaluronic acid to an aqueous suspension of the particles obtained in step c), and e) subjecting the mixture obtained in step d) to a cross-linking reaction with genipin, thereby producing the multifunctional hydrogel hybrid material.

2. The method according to claim 1, wherein functionalizing said silica particles with amino groups is carried out by the sol-gel method.

3. A multifunctional hydrogel hybrid material obtained by a method as defined in claim 1.

4. A multifunctional hydrogel hybrid material obtained by a method as defined in claim 2.

5. A method of treating bone losses in a subject in need thereof, the method comprising administering to the subject a therapeutically effective amount of the multifunctional hydrogel hybrid material as defined in claim 3.

6. The method according to claim 5, wherein the bone losses are due to osteoporosis.

7. The method according to claim 1, wherein suspending the silica particles obtained in step a) in an aqueous SBF solution is at a concentration of 1.5 M.

\* \* \* \* \*